US012582294B2

(12) United States Patent
Kobayashi

(10) Patent No.: US 12,582,294 B2
(45) Date of Patent: Mar. 24, 2026

(54) IMAGE PICKUP UNIT HAVING RESIN IN VIA HOLES FOR AN ENDOSCOPE

(71) Applicant: OLYMPUS CORPORATION, Tokyo (JP)

(72) Inventor: Keiichi Kobayashi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 279 days.

(21) Appl. No.: 18/515,781

(22) Filed: Nov. 21, 2023

(65) Prior Publication Data

US 2024/0088076 A1 Mar. 14, 2024

Related U.S. Application Data

(63) Continuation of application No. PCT/JP2021/030464, filed on Aug. 19, 2021.

(51) Int. Cl.
H01L 23/00 (2006.01)
A61B 1/00 (2006.01)
(Continued)

(52) U.S. Cl.
CPC ............ H01L 24/05 (2013.01); A61B 1/0011 (2013.01); A61B 1/051 (2013.01); H01L 24/08 (2013.01); H01L 24/13 (2013.01); H01L 24/16 (2013.01); H10F 39/12 (2025.01); H10F 39/811 (2025.01); H10F 77/93 (2025.01);
(Continued)

(58) Field of Classification Search
CPC ......... H01L 24/05; H01L 24/08; H01L 24/13; H01L 24/16; H10F 39/811; H10F 39/12; H10F 77/93; A61B 1/0011; A61B 1/051
See application file for complete search history.

(56) References Cited

U.S. PATENT DOCUMENTS 8,063,462 B2 11/2011 Tanida et al.
10,249,672 B2 * 4/2019 Fujimori ............... H01L 25/042
(Continued)

FOREIGN PATENT DOCUMENTS

CN 104900607 A * 9/2015 ....... H01L 21/76898
EP 1 154 471 A1 11/2001
(Continued)

OTHER PUBLICATIONS

International Search Report dated Nov. 9, 2021 received in PCT/JP2021/030464.

*Primary Examiner* — Alonzo Chambliss

(74) *Attorney, Agent, or Firm* — Scully, Scott, Murphy & Presser, P.C.

(57) ABSTRACT

An image pickup unit includes: an image pickup substrate including a first principal surface and a second principal surface, a light receiving circuit being formed on the first principal surface and a through wiring being placed on an inner surface of a via hole including an opening in the second principal surface; a solder resist film placed around the via hole on the second principal surface and in the via hole in a range from a bottom face to a level not reaching the second principal surface; and a bonding terminal which is made of solder, covers a surface of the solder resist film placed in the via hole, and is bonded to the through wiring on an outer edge of the opening in the via hole, the through wiring being not covered with the solder resist film.

10 Claims, 9 Drawing Sheets

(51) Int. Cl.

| | |
|---|---|
| *A61B 1/05* | (2006.01) |
| *H10F 39/00* | (2025.01) |
| *H10F 39/12* | (2025.01) |
| *H10F 77/00* | (2025.01) |

(52) U.S. Cl.
CPC ................. *H01L 2224/0219* (2013.01); *H01L 2224/0311* (2013.01); *H01L 2224/0345* (2013.01); *H01L 2224/0346* (2013.01); *H01L 2224/0401* (2013.01); *H01L 2224/05144* (2013.01); *H01L 2224/05147* (2013.01); *H01L 2224/05155* (2013.01); *H01L 2224/05541* (2013.01); *H01L 2224/05558* (2013.01); *H01L 2224/05624* (2013.01); *H01L 2224/05644* (2013.01); *H01L 2224/05647* (2013.01); *H01L 2224/05655* (2013.01); *H01L 2224/131* (2013.01)

(56) References Cited

U.S. PATENT DOCUMENTS

| | | | |
|---|---|---|---|
| 2001/0049187 A1 | 12/2001 | Enomoto et al. | |
| 2007/0241457 A1* | 10/2007 | Ida | H01L 21/76898 |
| | | | 257/E21.597 |
| 2012/0056291 A1 | 3/2012 | Suzuki et al. | |
| 2014/0312506 A1* | 10/2014 | Hayashi | H01L 21/3065 |
| | | | 257/774 |
| 2016/0099210 A1 | 4/2016 | Kwon et al. | |

FOREIGN PATENT DOCUMENTS

| | | | |
|---|---|---|---|
| EP | 1 942 523 A1 | 7/2008 | |
| JP | 2000-174050 A | 6/2000 | |
| JP | 2004-200398 A | 7/2004 | |
| JP | 4693827 B2 | 6/2011 | |
| JP | 2012-059881 A | 3/2012 | |
| WO | 2000/019517 A1 | 4/2000 | |
| WO | 2021/186519 A1 | 9/2021 | |

* cited by examiner

IMAGE PICKUP UNIT HAVING RESIN IN VIA HOLES FOR AN ENDOSCOPE

CROSS REFERENCE TO RELATED APPLICATION

This application is a continuation application of PCT/JP2021/030464 filed on Aug. 19, 2021, the entire contents of which are incorporated herein by this reference.

BACKGROUND OF THE INVENTION

1. Field of the Invention

The present invention relates to a semiconductor apparatus in which resin is placed in via holes in a semiconductor substrate, an image pickup unit in which resin is placed in via holes in an image pickup substrate, an endoscope that includes the image pickup unit in which the resin is placed in the via holes in the image pickup substrate, and a method for manufacturing the semiconductor apparatus in which the resin is placed in the via holes in the semiconductor substrate.

2. Description of the Related Art

The specification of U.S. Pat. No. 8,063,462 discloses a semiconductor apparatus in which through wirings are provided in through-holes in a semiconductor substrate. The through-holes are filled with the through wirings made of metal. Solder bumps, which are external electrodes, are placed in extension members of the through wirings.

SUMMARY OF THE INVENTION

A semiconductor apparatus according to an embodiment includes: a semiconductor substrate including a first principal surface and a second principal surface on a side opposite the first principal surface, a semiconductor circuit being formed on the first principal surface and a through wiring electrically continuous with the semiconductor circuit being placed on an inner surface of a via hole including an opening in the second principal surface; resin placed around the via hole on the second principal surface and in the via hole in a range from a bottom face to a level not reaching the second principal surface; and a bonding terminal which is made of solder, covers a surface of the resin placed in the via hole, and is bonded to the through wiring on an outer edge of the opening in the via hole, the through wiring being not covered with the resin.

An image pickup unit according to an embodiment includes: a semiconductor substrate including a first principal surface and a second principal surface on a side opposite the first principal surface, a light-receiving circuit being formed on the first principal surface and a through wiring electrically continuous with the light-receiving circuit being placed on an inner surface of a via hole including an opening in the second principal surface; resin placed around the via hole on the second principal surface and in the via hole in a range from a bottom face to a level not reaching the second principal surface; and a bonding terminal which is made of solder, covers a surface of the resin placed in the via hole, and is bonded to the through wiring on an outer edge of the opening in the via hole, the through wiring being not covered with the resin.

An endoscope according to an embodiment includes an image pickup unit; and an insertion portion including the image pickup unit in a distal end portion. The image pickup unit includes: a semiconductor substrate including a first principal surface and a second principal surface on a side opposite the first principal surface, a light-receiving circuit being formed on the first principal surface and a through wiring electrically continuous with the light-receiving circuit being placed on an inner surface of a via hole including an opening in the second principal surface, resin placed around the via hole on the second principal surface and in the via hole in a range from a bottom face to a level not reaching the second principal surface, and a bonding terminal which is made of solder, covers a surface of the resin placed in the via hole, and is bonded to the through wiring on an outer edge of the opening in the via hole, the through wiring being not covered with the resin.

A method for manufacturing a semiconductor apparatus according to an embodiment includes: producing a semiconductor substrate including a first principal surface and a second principal surface on a side opposite the first principal surface, a semiconductor device and an electrode connected to the semiconductor device being placed on the first principal surface; forming a via hole reaching the electrode, in the second principal surface; placing a through wiring on an inner surface of the via hole; coating part of the second principal surface which is around the via hole and an interior of the via hole in a range from a bottom face to a level not reaching the second principal surface with resin; and installing a bonding terminal which is made of solder, covers a surface of the resin in the via hole, and is bonded to the through wiring in an upper part of the via hole.

DETAILED DESCRIPTION OF THE PREFERRED EMBODIMENTS

First Embodiment

In the following description, the drawings based on each embodiment are schematic, and a relationship between thickness and width of each component as well as thickness ratios and relative angles among individual components are different from actual ones. Some of dimensional relationships or ratios may differ among the drawings. Illustrations of some components are omitted. The direction from which light enters is designated as an upper direction.

Figure 1:
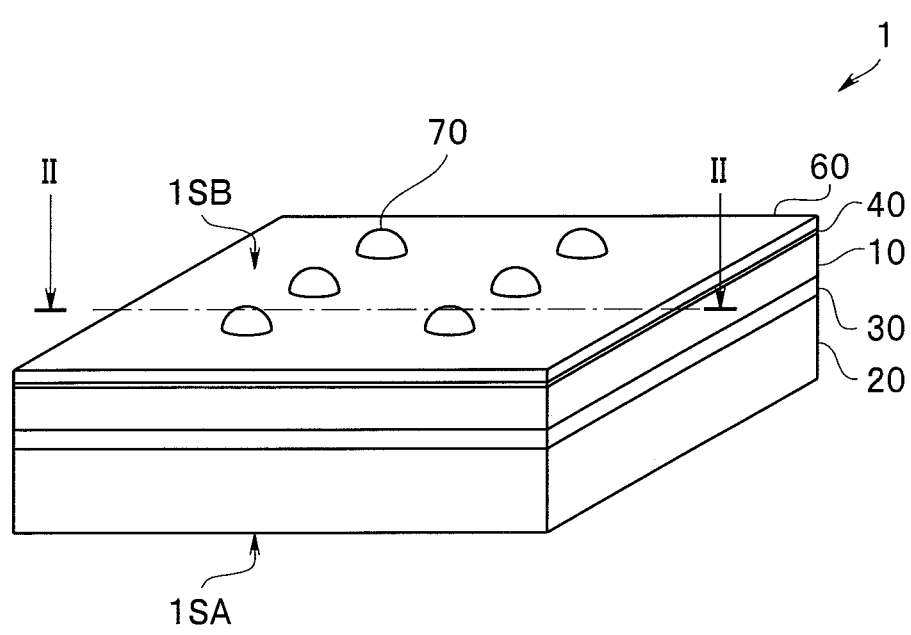
FIG. 1 is a perspective view of an image pickup unit according to a first embodiment.
Figure 2:
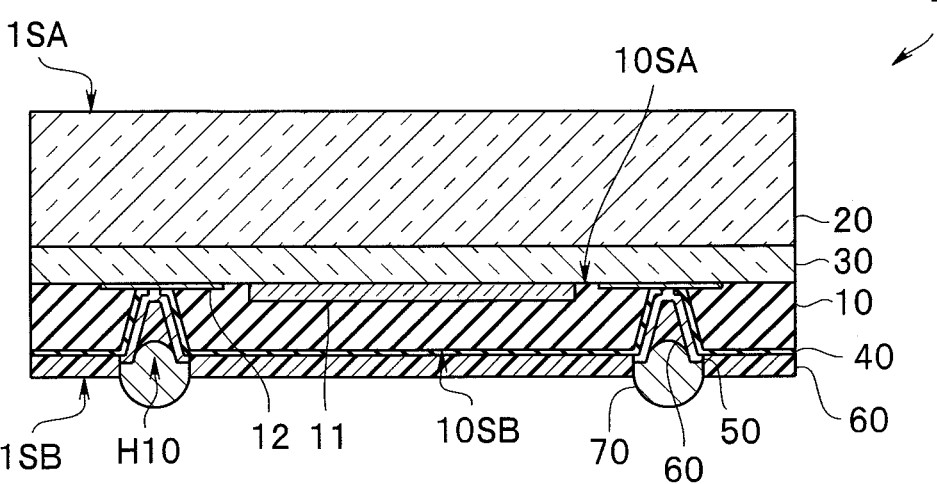
FIG. 2 is a cross-sectional view taken along line II-II in FIG. 1.

As shown in FIGS. 1 and 2, an image pickup unit 1 according to the present embodiment is a semiconductor apparatus that includes an image pickup substrate 10, which is a semiconductor substrate, and cover glass 20. The image pickup substrate 10 includes a first principal surface 10SA, which is a light receiving surface, and a second principal surface 10SB on a side opposite the first principal surface 10SA. A light receiving circuit 11, which is a semiconductor circuit, is formed and an electrode 12 connected to the light receiving circuit 11 is placed on the first principal surface 10SA. The cover glass 20 is adhered to the first principal surface 10SA of the image pickup substrate 10 via a transparent adhesive layer 30. An upper surface 1SA of the image pickup unit 1 is made up of the cover glass 20.

A rear surface of the electrode 12 placed on the first principal surface 10SA is exposed to a bottom face of a via hole H10 that has an opening in the second principal surface 10SB of the image pickup substrate 10. In other words, the via hole H10 is a closed-end hole. An insulating layer 40 is placed on an inner surface of the via hole H10 and a through wiring 50 is placed on the insulating layer 40. The through wiring 50 is electrically connected to the light receiving circuit 11 through an opening in the insulating layer 40 on the bottom face of the via hole H10 and through the electrode 12.

Note that when the image pickup substrate 10 is a stacked substrate made up of a plurality of semiconductor devices, an undersurface of the lowermost semiconductor device is the second principal surface 10SB.

Resin 60, which is a solder resist, is placed on the second principal surface 10SB of the image pickup substrate 10. The resin 60 is a heat-resistant resin used to prevent solder from attaching to parts where it is not needed. An undersurface 1SB of the image pickup unit 1 is made of the resin 60. The resin 60 is placed around the via hole H10 on the second principal surface 10SB and in the via hole H10 in a range from a bottom face to a level not reaching the second principal surface 10SB. In other words, the through wiring 50 in an upper part of the via hole H10 includes an annular exposed area not covered with the resin 60.

A bonding terminal 70 made of solder covers a surface of the resin 60 placed in the via hole H10 and is bonded to the through wiring 50 in the exposed area not covered with the resin 60 in the upper part of the via hole H10.

The image pickup unit 1 makes it easy to place the resin 60 in the via hole H10, and the bonding terminal 70 is placed right above the via hole H10. Consequently, the image pickup unit 1 is small and high in reliability.

Note that even if a semiconductor apparatus includes a semiconductor substrate on which a semiconductor circuit is formed and in which resin is placed in a via hole, needless to say, the semiconductor apparatus has same effects as the image pickup unit 1 as long as the semiconductor apparatus includes a bonding terminal which is made of solder, covers the surface of the resin placed in the via hole, and is bonded to a through wiring on an outer edge of an opening in the via hole, the through wiring being not covered with the resin.

\<Method for Manufacturing Image Pickup Unit\>

Figure 3:
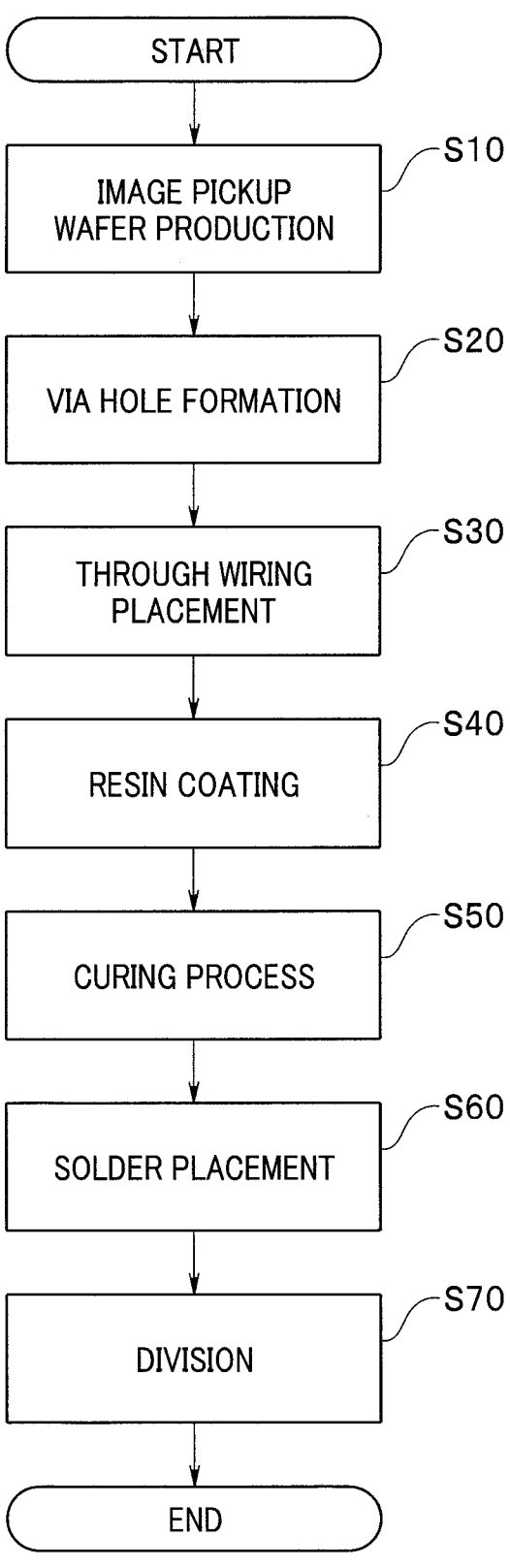
FIG. 3 is a flowchart of a method for manufacturing the image pickup unit according to the first embodiment.

A method for manufacturing the image pickup unit 1 will be described with reference to a flowchart of FIG. 3.

\<Step S10\> Image Pickup Wafer Production

An image pickup wafer 10W including a plurality of semiconductor substrates is produced using a publicly known semiconductor manufacturing technique that involves forming a plurality of light receiving circuits 11 on the first principal surface 10SA of a silicon wafer and placing a plurality of electrodes connected to the respective light receiving circuits 11. The light receiving circuits 11 are CMOS (complementary metal oxide semiconductor) light receiving circuits or CCDs (charge coupled devices).

Then, a glass wafer 20W is adhered to the first principal surface 10SA using an adhesive layer 30W. It is sufficient that the glass wafer 20W is transparent in a wavelength band of light used for image pickup, and the glass wafer 20W is made, for example, of borosilicate glass, quartz glass, single-crystal sapphire, or other glass.

The adhesive layer 30W is made of a BCB (benzocyclobutene) resin, an epoxy-based resin, a silicone-based resin, or the like, which has properties such as high transparency (e.g., transmittance at visible wavelengths is 90% or above), high adhesive strength, and high resistance to heat or the like in downstream operations. Regarding a curing method of the adhesive layer 30W, as long as predetermined characteristics are satisfied, any of a heat curing method, a UV curing method, a UV curing method+a heat curing method, a UV curing method+a moisture curing method, and a cold setting method may be used depending on the resin.

Figure 4A:
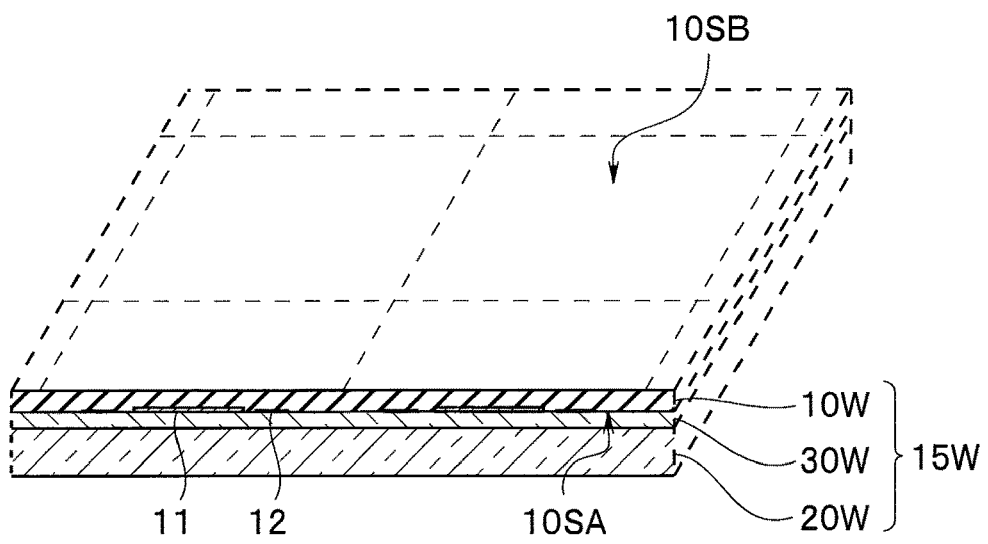
FIG. 4A is a perspective cross-sectional view for explaining the method for manufacturing the image pickup unit according to the first embodiment.
Figure 4B:
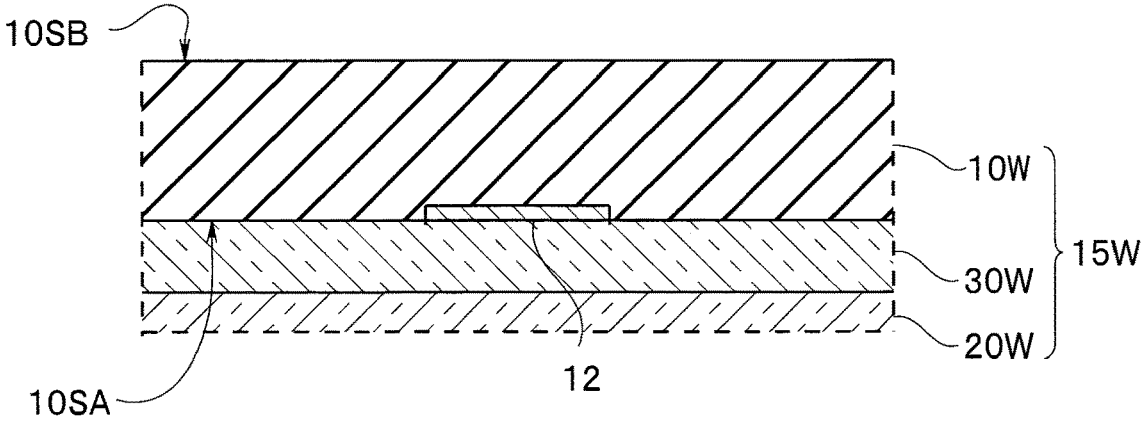
FIG. 4B is a partial cross-sectional view of FIG. 4A.

FIG. 4A shows a stacked wafer 15W in which the glass wafer 20W is adhered to the image pickup wafer 10W via the adhesive layer 30W. Subsequent steps are carried out with respect to the second principal surface 10SB of the image pickup wafer 10W. FIG. 4B is an enlarged cross-sectional view of part of FIG. 4A.

Note that after the glass wafer 20W is adhered, preferably the image pickup wafer 10W is made thin by grinding or the like.

\<Step S20\> Via Hole Formation

Figure 5A:
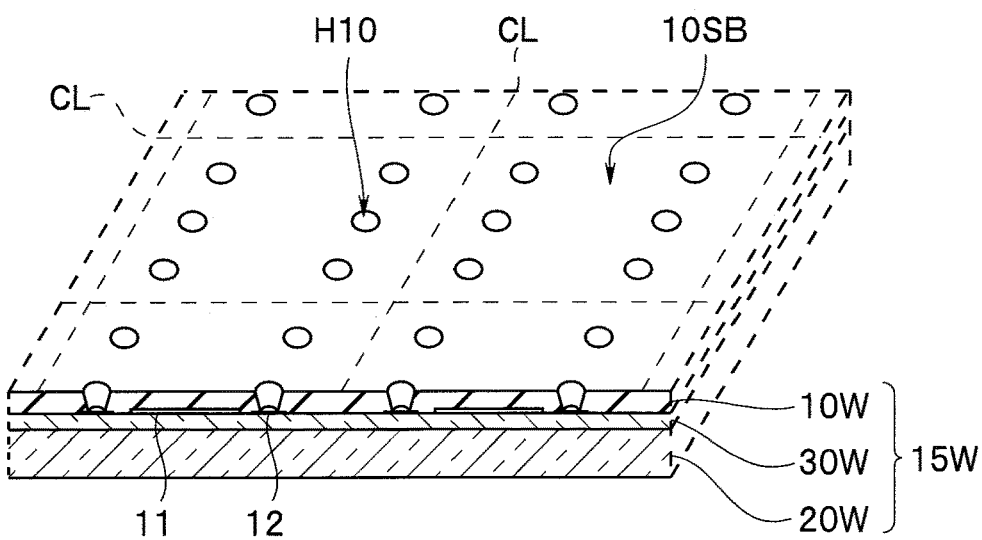
FIG. 5A is a perspective cross-sectional view for explaining the method for manufacturing the image pickup unit according to the first embodiment.
Figure 5B:
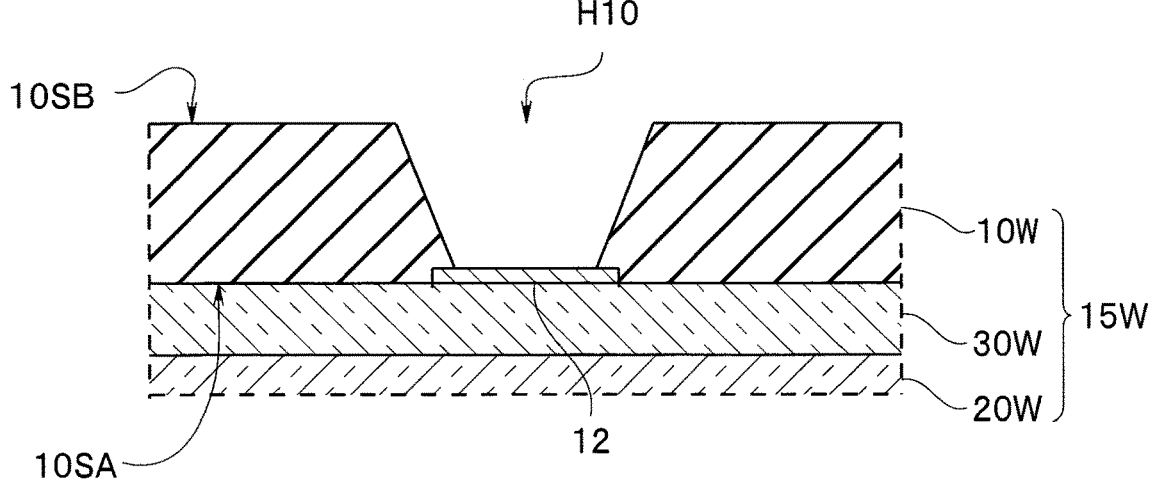
FIG. 5B is a partial cross-sectional view of FIG. 5A.

As shown in FIGS. 5A and 5B, the via holes H10 are formed in the second principal surface 10SB of the stacked wafer 15W such that the electrodes 12 form bottom faces of the via holes, respectively. Although not illustrated, an etching process is performed after an etching mask is placed on the second principal surface 10SB. The etching mask is an inorganic film such as a silicon oxide film or a silicon nitride film, or an organic film of photoresist, polyimide, BCB, or the like.

In the etching process, the via holes H10 are formed, for example, by wet etching using an alkaline solution such as KOH or TMAH or by dry etching using ICP-RIE.

The electrodes 12 serve as etch-stop layers for the via holes H10. Depth of the via holes H10, i.e., thickness of the image pickup wafer 10W, is, for example, 60 μm.

<Step S30> Through Wiring Placement

Figure 6:
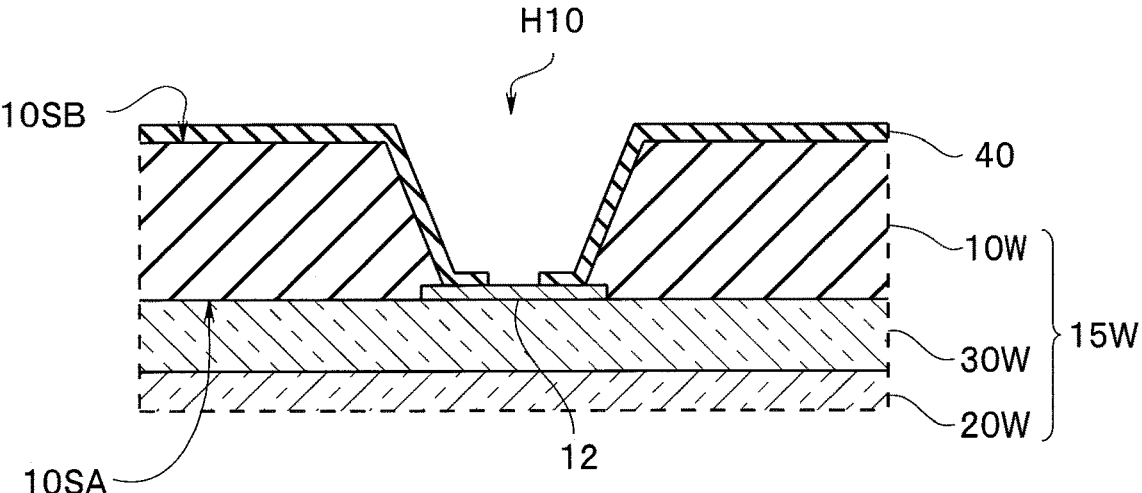
FIG. 6 is a partial cross-sectional view for explaining the method for manufacturing the image pickup unit according to the first embodiment.

As shown in FIG. 6, the insulating layer 40 made of an inorganic material is placed. The insulating layer 40 is 0.1 μm to 3 μm thick. The insulating layer 40 is, for example, a silicon oxide film or a silicon nitride film formed using plasma CVD, photo-CVD, or the like. Tetraethoxy silane (TEOS), octamethylcyclotetrasiloxane (OMCTS), or the like is used as a source gas in forming a silicon oxide film. In forming a silicon nitride film, a mixed gas such as $SiH_4+NH_3$, $SiH_2CL_2+NH_3$, $SiH_4+N_2$, or $SiH_4+NH_3+N_2$ is used as a source gas.

Openings are formed in the insulating layer 40 on the bottom faces of the via holes H10 using, for example, an ion milling process.

Figure 7:
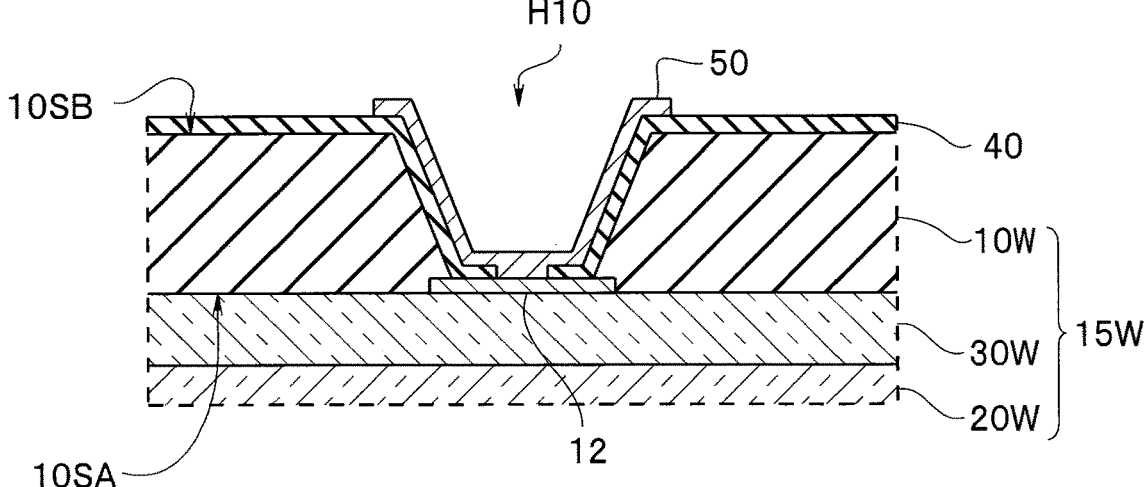
FIG. 7 is a partial cross-sectional view for explaining the method for manufacturing the image pickup unit according to the first embodiment.

Then, as shown in FIG. 7, the through wirings 50 are placed on the inner surfaces of the via holes H10, covering the insulating layer 40. A conductor layer, which is made of aluminum or copper, is formed on the entire second principal surface 10SB using, for example, a sputtering process or a vapor deposition process, and then undergoes patterning. Preferably, the through wirings 50 are annularly extended around the via holes H10 on the second principal surface 10SB. The through wirings 50 may be extended further from the areas in which the through wirings 50 are extended annularly.

The through wirings 50 may be placed using a plating process after a seed layer made of a conductor is placed by the sputtering process or the vapor deposition process. The through wirings 50 are 2 μm to 15 μm thick. For example, a nickel layer and a gold layer may be formed as solder barrier layers on a conductor layer made of copper.

<Step S40> Resin Coating

A solder resist film 60, which is a resin, is applied to the second principal surface 10SB by a spin coating process. The solder resist, which contains a solvent and has fluidity, flows into the via holes H10 from around the via holes H10. Consequently, right after the application, almost no solder resist film 60 or an extremely thin solder resist film is placed on outer edges of openings in the via holes H10.

In a normal solder resist application method, using a leveling action produced by leaving the solder resist at rest for a predetermined period of time after the application, preferably, the solder resist film 60 is placed such that the entire undersurface 1SB will become level including areas covering the via holes H10.

Figure 8:
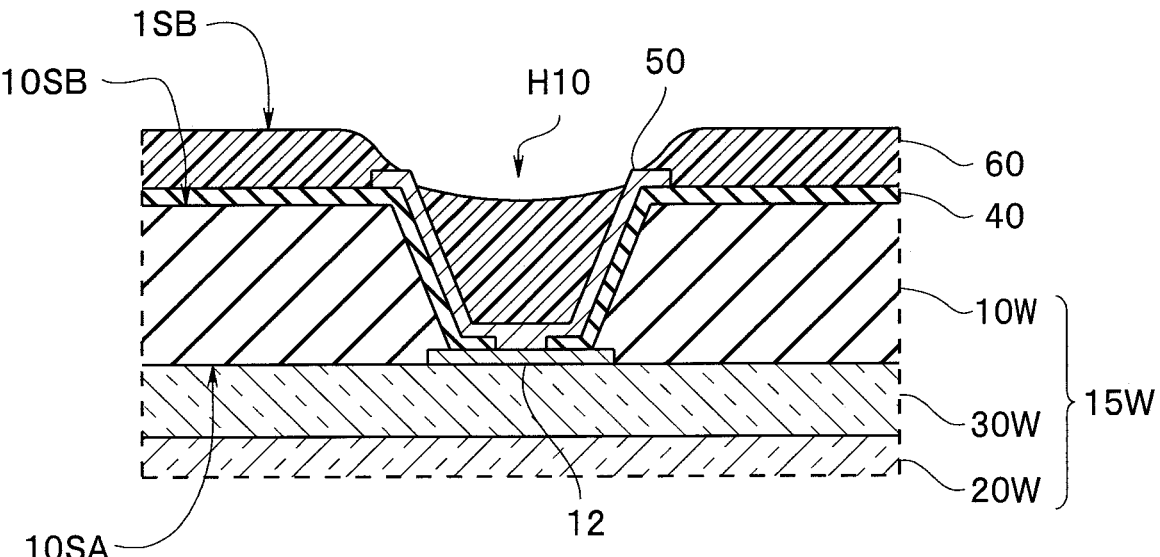
FIG. 8 is a partial cross-sectional view for explaining the method for manufacturing the image pickup unit according to the first embodiment.

In contrast, with the manufacturing method according to the present embodiment, as shown in FIG. 8, the solder resist film 60 is placed such that the areas covering the via holes H10 in the undersurface 1SB will become concave. If a solder resist less prone to leveling is used, if the solvent remaining right after the application is evaporated in a short period of time, or if coating conditions are optimized, the through wirings 50 will have annular areas not covered with the solder resist film 60 on outer edges of the via holes H10.

By removing the solder resist film 60 on the outer edges of the via holes H10 using a photosensitive solder resist, areas not covering the through wirings 50 may be formed on the solder resist film 60.

<Step S50> Curing Process

A heat curing process of the solder resist film 60 is performed. For example, the solder resist film 60, which is made of heat curing epoxy resin shrinks as a result of the curing process. After the curing process, the solder resist film 60 on the second principal surface 10SB is 1 μm to 30 μm thick.

Figure 9:
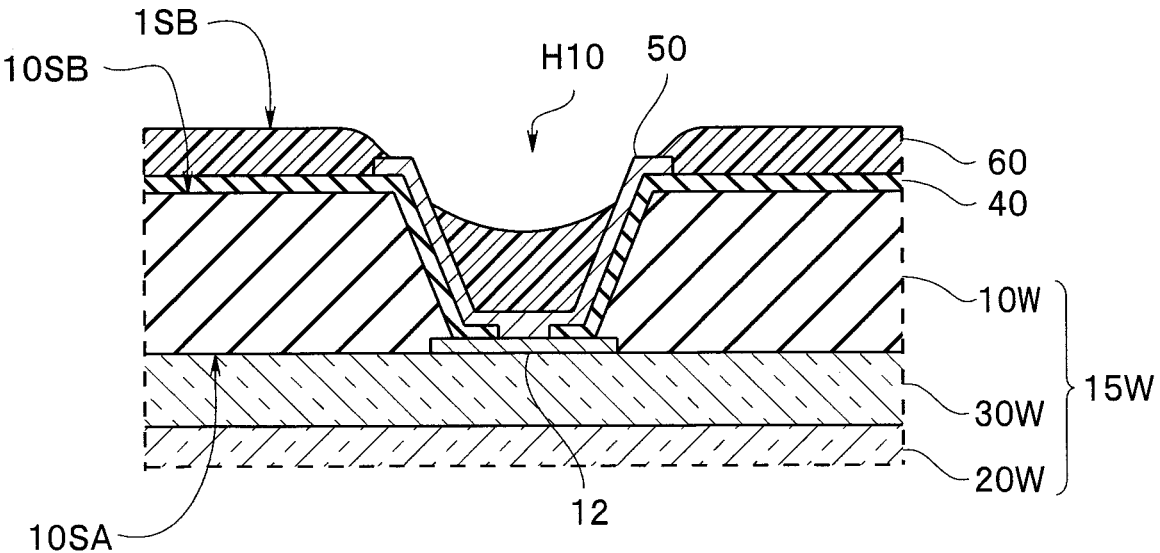
FIG. 9 is a partial cross-sectional view for explaining the method for manufacturing the image pickup unit according to the first embodiment.

The widths of the annular areas of the through wirings 50 which are not covered with the solder resist film 60 are larger after the curing process (FIG. 9) than before the curing (FIG. 8). The solder resist film 60 placed in the via holes H10 has concave surfaces.

Preferably, an ashing process is performed after the curing process to reduce thickness of the solder resist film 60. The ashing process makes it possible to increase the width of the annular areas of the through wirings 50 not covered with the solder resist film 60 or remove the solder resist film 60 remaining in part of the annular areas.

<Step S60> Solder Placement

Figure 10:
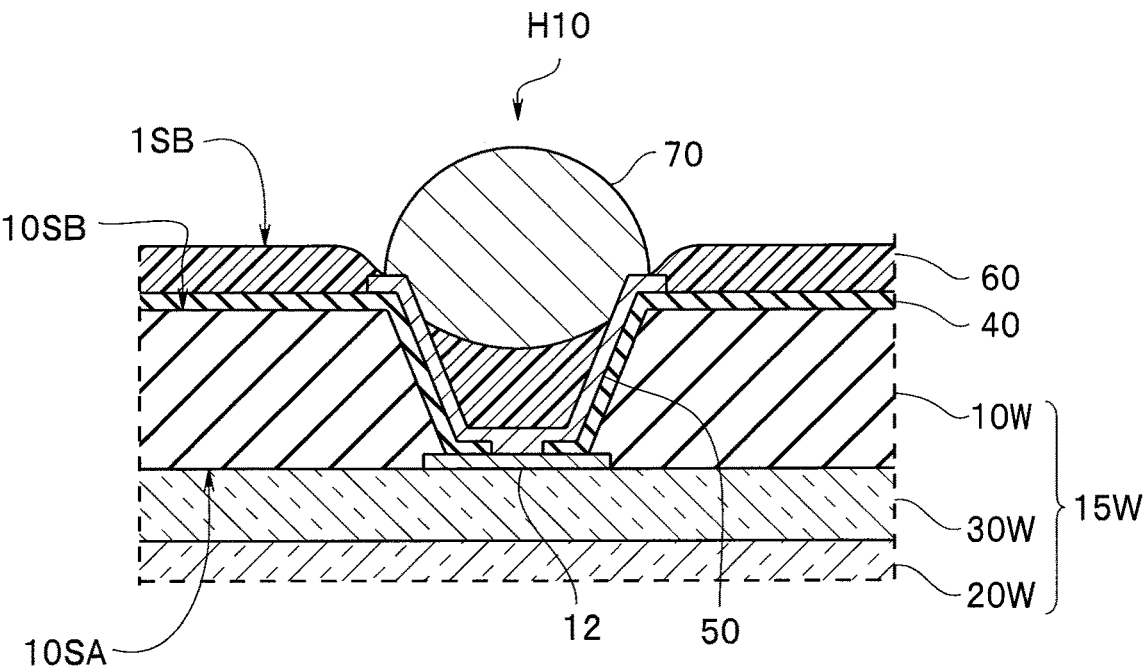
FIG. 10 is a partial cross-sectional view for explaining the method for manufacturing the image pickup unit according to the first embodiment.

As shown in FIG. 10, a bonding terminal 70 made of solder and used for bonding to a wiring board is placed in each of the via holes H10. For example, a solder ball or solder paste is used for the bonding terminal 70. A solder ball having a metal core made of copper may be used as the bonding terminal 70.

As a result of a reflow process, the solder put in the via hole H10 becomes the bonding terminal 70, which being convex in shape, covers the surface of the solder resist film 60 placed in the via hole H10. On the outer edge of the opening in the via hole H10, the bonding terminal 70 is bonded to the annular area of the through wiring 50 not covered with the solder resist film 60.

<Step S70> Division

Figure 11:
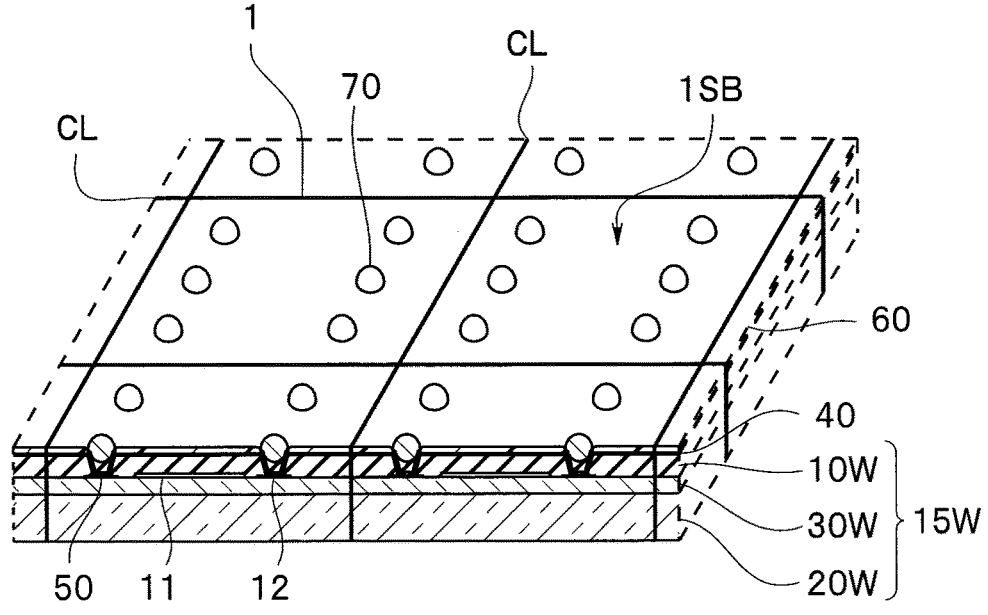
FIG. 11 is a perspective cross-sectional view for explaining the method for manufacturing the image pickup unit according to the first embodiment.

As shown in FIG. 11, the stacked wafer 15W is cut by the cutting lines CL and thereby divided into a plurality of the image pickup units 1.

By adhering a stacked lens wafer including a plurality of lens units to the glass wafer 20W before a cutting step, the stacked wafer 15W may be cut together with the stacked lens wafer.

The method for manufacturing the image pickup unit 1 according to the present embodiment can easily manufacture the image pickup unit that is small and high in reliability.

Modifications of First Embodiment

Image pickup units 1A and 1B according to modifications of the first embodiment are similar to the image pickup unit 1 and have the same effects as the image pickup unit 1. Therefore, in the following description, components having the same functions as the image pickup unit 1 are denoted by the same reference numerals as the corresponding components of the image pickup unit 1, and description thereof will be omitted.

Figure 12:
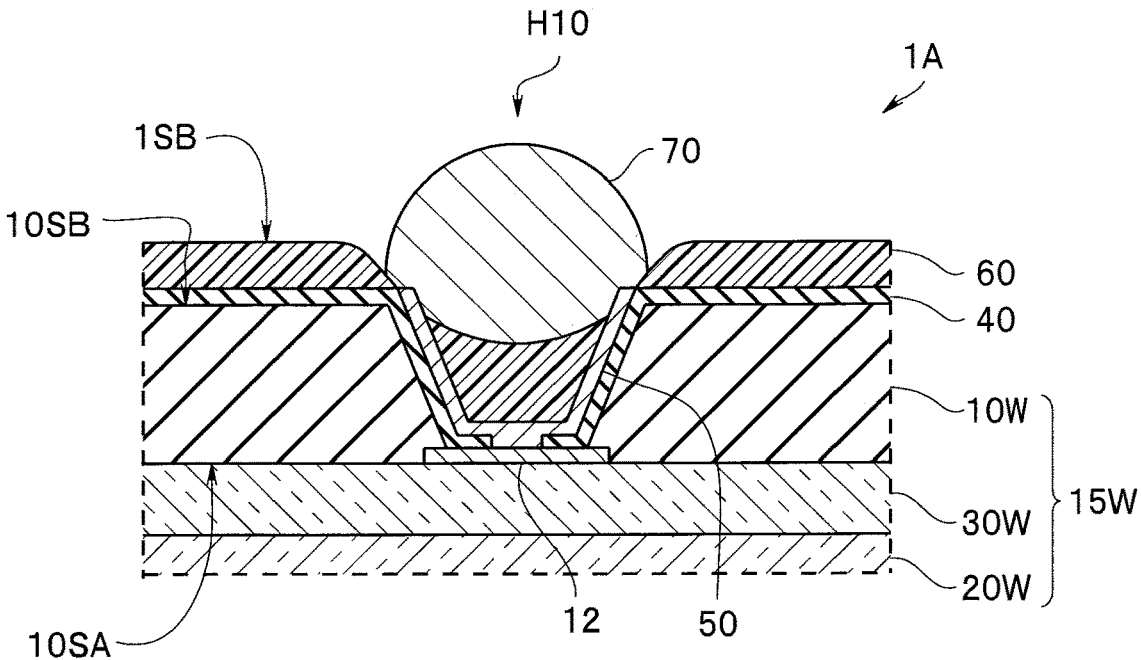
FIG. 12 is a partial cross-sectional view of an image pickup unit according to Modification 1 of the first embodiment.

In the image pickup unit 1A according to Modification 1 shown in FIG. 12, an end face of the through wiring 50 is flush with the second principal surface 10SB, more precisely, with a surface of the insulating layer 40.

Figure 13:
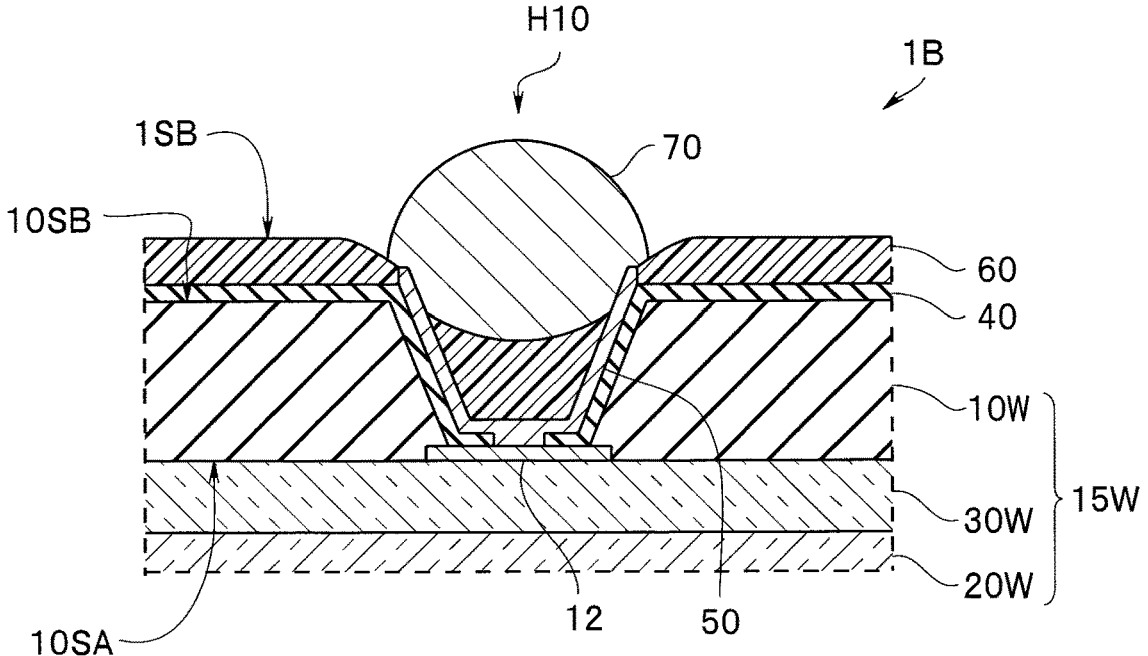
FIG. 13 is a partial cross-sectional view of an image pickup unit according to Modification 2 of the first embodiment.

In an image pickup unit 1B according to Modification 2 shown in FIG. 13, the end face of the through wiring 50 protrudes from the second principal surface 10SB, but is not extended to the second principal surface 10SB.

Second Embodiment

Figure 14:
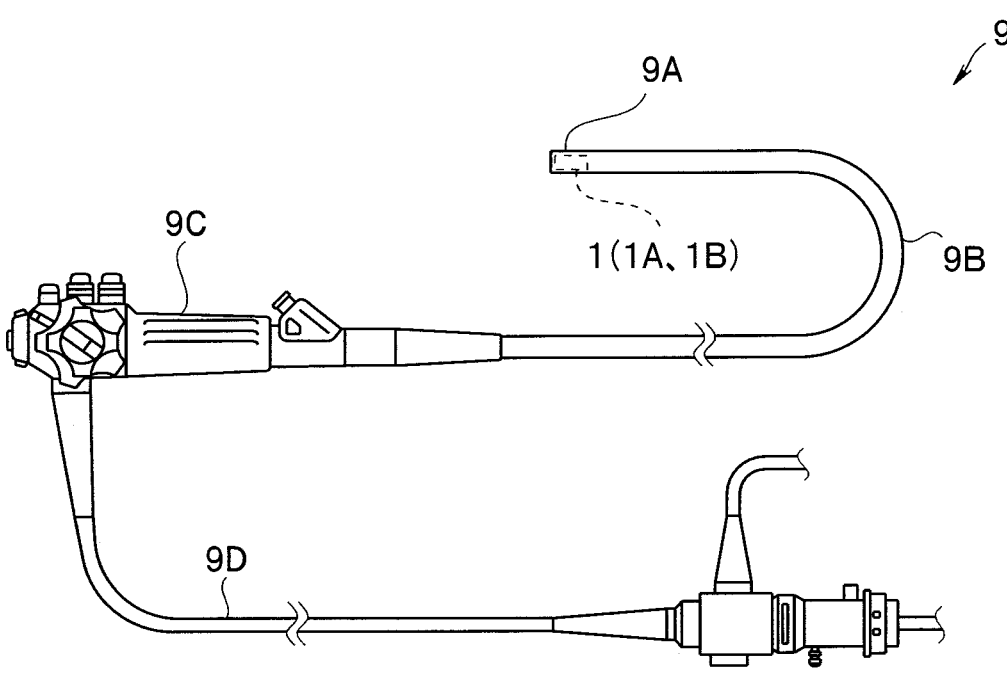
FIG. 14 is a perspective view of an endoscope according to a second embodiment.

As shown in FIG. 14, an endoscope 9 according to the present embodiment includes a distal end portion 9A, an insertion portion 9B extended from the distal end portion 9A, an operation portion 9C disposed on a proximal end side of the insertion portion 9B, and a universal cord 9D extending from the operation portion 9C.

The image pickup unit 1 is disposed on the distal end portion 9A. An image pickup signal outputted from the image pickup unit 1 is transmitted to a processor (not shown) through a cable passing through the universal cord 9D. A drive signal from the processor to the image pickup unit 1 is also transmitted through a cable passing through the universal cord 9D.

As already described, the image pickup unit 1 is high in reliability and easy to manufacture. Consequently, the endoscope 9 is high in reliability and easy to manufacture as well.

The endoscope 9 may be either a flexible endoscope, the insertion portion 9B of which is flexible or a rigid endoscope, the insertion portion 9B of which is rigid. The use of the endoscope 9 may be either medical or industrial.

The present invention is not limited to the embodiments and the like described above, and various alterations, combinations, and applications are possible without departing from the gist of the invention.

What is claimed is:

1. A semiconductor apparatus comprising:
a semiconductor substrate including a first principal surface and a second principal surface on a side opposite the first principal surface, a semiconductor circuit being formed on the first principal surface and a through wiring electrically continuous with the semiconductor circuit being placed on an inner surface of a via hole including an opening in the second principal surface;
resin placed around the via hole on the second principal surface and in the via hole in a range from a bottom face to a level not reaching the second principal surface; and
a bonding terminal which is made of solder, covers a surface of the resin placed in the via hole, and is bonded to the through wiring on an outer edge of the opening in the via hole, the through wiring being not covered with the resin.

2. The semiconductor apparatus according to claim 1, wherein:
the through wiring is extended to around the via hole; and
the bonding terminal is bonded to the through wiring which is located around the via hole and is not covered with the resin.

3. The semiconductor apparatus according to claim 1, wherein the surface of the resin placed in the via hole is concave.

4. The semiconductor apparatus according to claim 1, wherein the through wiring that is not covered with the resin is annular.

5. The semiconductor apparatus according to claim 1, wherein the resin is a solder resist.

6. An image pickup unit comprising:
a semiconductor substrate including a first principal surface and a second principal surface on a side opposite the first principal surface, a light-receiving circuit being formed on the first principal surface and a through wiring electrically continuous with the light-receiving circuit being placed on an inner surface of a via hole including an opening in the second principal surface;

resin placed around the via hole on the second principal surface and in the via hole in a range from a bottom face to a level not reaching the second principal surface; and
a bonding terminal which is made of solder, covers a surface of the resin placed in the via hole, and is bonded to the through wiring on an outer edge of the opening in the via hole, the through wiring being not covered with the resin.

7. An endoscope comprising:
an image pickup unit; and
an insertion portion including the image pickup unit in a distal end portion,
wherein the image pickup unit includes:
a semiconductor substrate including a first principal surface and a second principal surface on a side opposite the first principal surface, a light-receiving circuit being formed on the first principal surface and a through wiring electrically continuous with the light-receiving circuit being placed on an inner surface of a via hole including an opening in the second principal surface,
resin placed around the via hole on the second principal surface and in the via hole in a range from a bottom face to a level not reaching the second principal surface, and
a bonding terminal which is made of solder, covers a surface of the resin placed in the via hole, and is bonded to the through wiring on an outer edge of the opening in the via hole, the through wiring being not covered with the resin.

8. A method for manufacturing a semiconductor apparatus comprising:
producing a semiconductor substrate including a first principal surface and a second principal surface on a side opposite the first principal surface, a semiconductor device and an electrode connected to the semiconductor device being placed on the first principal surface;
forming a via hole reaching the electrode, in the second principal surface;
placing a through wiring on an inner surface of the via hole;
coating part of the second principal surface which is around the via hole and an interior of the via hole in a range from a bottom face to a level not reaching the second principal surface with resin; and
installing a bonding terminal which is made of solder, covers a surface of the resin in the via hole, and is bonded to the through wiring in an upper part of the via hole.

9. The method for manufacturing a semiconductor apparatus according to claim 8, wherein the resin is placed using a spin coating process.

10. The method for manufacturing a semiconductor apparatus according to claim 9, wherein after application of the resin, the resin is cured.

* * * * *